United States Patent [19]
Yamamoto et al.

[11] 3,936,468
[45] Feb. 3, 1976

[54] PHENYLBUTANOL DERIVATIVES

[75] Inventors: Hisao Yamamoto, Nishinomiya; Masaru Nakao; Kikuo Sasajima, both of Toyonaka; Isamu Maruyama, Minoo; Shigenari Katayama, Takarazuka, all of Japan

[73] Assignee: Sumitomo Chemical Company, Ltd., Osaka, Japan

[22] Filed: Feb. 15, 1973

[21] Appl. No.: 332,777

Related U.S. Application Data

[62] Division of Ser. No. 82,100, Oct. 19, 1970, abandoned.

[30] Foreign Application Priority Data

| Oct. 27, 1969 | Japan | 44-86175 |
|---|---|---|
| Nov. 4, 1969 | Japan | 44-88513 |
| Feb. 3, 1970 | Japan | 45-9688 |
| Feb. 6, 1970 | Japan | 45-10930 |
| Feb. 9, 1970 | Japan | 45-11629 |
| Apr. 17, 1970 | Japan | 45-33362 |

[52] U.S. Cl. 260/293.84; 260/247.5 G; 260/293.6; 260/293.64; 260/293.67; 260/293.68; 260/293.69; 260/293.71; 260/293.76; 260/293.78; 260/293.8; 260/293.83; 260/294.8 D; 260/295 K; 260/296 R; 260/297 R; 424/248; 424/263; 424/267

[51] Int. Cl.² ..................... C07D 211/52

[58] Field of Search .......... 260/293.8, 293.84

[56] References Cited
UNITED STATES PATENTS

| 3,080,372 | 3/1963 | Janssen | 260/293.8 |
|---|---|---|---|
| 3,438,991 | 4/1969 | Janssen | 260/293.8 |
| 3,462,444 | 8/1969 | Beckett et al. | 260/293.84 |

OTHER PUBLICATIONS

Chemical Abstracts 64:5037g (1966) Moehrle.
Intl. J. Neuropharmacol, 1:145–148 (1962) Janssen.
J. Med. & Pharm. Chem. 2:31–45 (1960) Janssen et al.

*Primary Examiner*—Sherman D. Winters
*Attorney, Agent, or Firm*—Stevens, Davis, Miller & Mosher

[57] ABSTRACT

Butyrophenone derivatives having excellent psychotropic activity and represented by the formula,

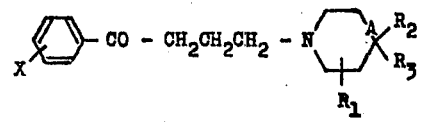

wherein A represents a single or double bond linkage; $R_1$ represents a hydrogen atom or a $C_1 - C_4$ alkyl group; $R_2$, which is present only in case A represents a single bond linkage, represents a hydrogen atom, or a hydroxyl, $C_1 - C_4$ alkyl, or $C_1 - C_4$ alkoxy group; $R_3$ represents a hydrogen atom, or a piperidino, pyrrolidino, morpholino, furyl, thienyl, $C_1 - C_4$ alkylamino, benzylamino, unsubstituted or halogen-substituted phenyl group, etc.; and X represents a hydrogen or halogen atom, or a $C_1 - C_4$ alkyl, $C_1 - C_4$ alkoxy, or trifluoromethyl group, can be prepared by reducing a benzoylpropionamide derivative of the formula,

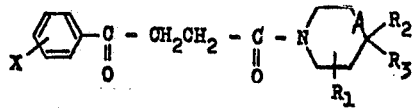

wherein A, $R_1$, $R_2$, $R_3$ and X have the same meanings as defined above, to a phenylbutanol derivative of the formula,

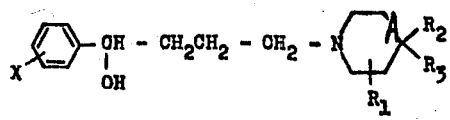

4 Claims, No Drawings

PHENYLBUTANOL DERIVATIVES

This is a division of application Ser. No. 82,100, filed Oct. 19, 1970, now abandoned.

The present invention relates to a process for preparing butyrophenone derivatives useful as medicines. More particularly, the invention relates to a novel and advantageous process for preparing butyrophenone derivatives represented by the general formula,

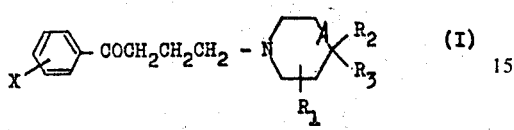

wherein
A signifies a single or double bond linkage;
$R_1$ signifies a hydrogen atom or a $C_1 - C_4$ alkyl group;
$R_2$, which is present only in case A signifies a single bond linkage, signifies a hydrogen atom, or a hydroxyl, $C_1 - C_4$ alkyl or $C_1 - C_4$ alkoxy group;
$R_3$ signifies a hydrogen atom, or a piperidino, pyrrolidino, morpholino, furyl, thienyl, $C_1 - C_4$ alkylamino, benzylamino, unsubstituted or substituted phenyl group having the formula,

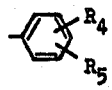

(wherein each of $R_4$ and $R_5$ signifies a hydrogen or halogen atom, or a $C_1 - C_4$ alkyl, $C_1 - C_4$ alkoxy, or trifluoromethyl group), or a group having the formula,

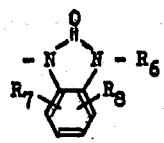

(wherein $R_6$ signifies a hydrogen atom or a $C_1 - C_4$ alkyl group, and each of $R_7$ and $R_8$ signifies a hydrogen or halogen atom, a $C_1 - C_4$ alkyl, or $C_1 - C_4$ alkoxy group); and
X signifies a hydrogen or halogen atom, or a $C_1 - C_4$ alkyl, $C_1 - C_4$ alkoxy, or trifluoromethyl group.

The butyrophenone derivatives represented by the above-said general formula (I), which are prepared by the process of the present invention, have an excellent central nervous system depressant and are useful as tranquilizers, analgesics, and sedatives. For example, γ-(4-hydroxy-4-p-chlorophenylpiperidino)-p-fluorobutyrophenone is known in the art as a substance having an excellent psychotropic activity.

The present inventors have found a novel and advantageous process for preparing these useful butyrophenone derivatives. That is, the present inventors have found that the butyrophenone derivatives of the above-said formula (I) can be prepared very advantageously by the following reactions:

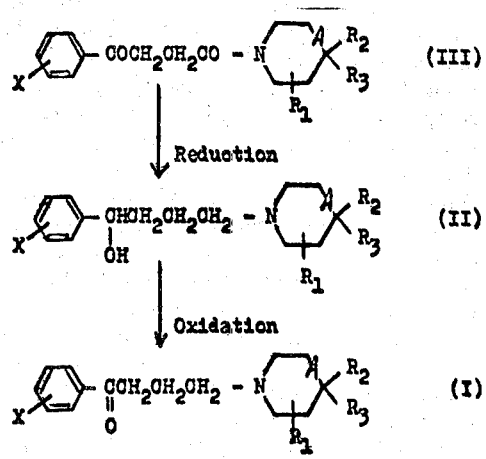

wherein A, $R_1$, $R_2$, $R_3$ and X have the same meanings as mentioned above.

Accordingly, the first object of this invention is to provide a novel and advantageous process for preparing butyrophenone derivatives of the above-said general formula (I).

Another object is to provide novel phenylbutanol derivatives useful as medicines or intermediates for medicines.

A further object is to provide a novel pharmaceutical composition.

Other objects and merits of the present invention will be apparent from the following description.

In order to attain the above-mentioned objects, the present invention provides a process for preparing butyrophenone derivatives of the general formula (I), which is characterized by reacting a phenylbutanol derivative of the general formula (II) with an oxidizing agent.

Further, the present invention provides a process for preparing butyrophenone derivatives of the general formula (I), which is characterized by reacting a benzoylpropionamide derivative of the general formula (III) with a reducing agent to form a phenylbutanol derivative of the general formula (II), and then reacting the said phenylbutanol derivative of the general formula (II) with an oxidizing agent.

Moreover, the present invention provides novel phenylbutanol derivatives represented by the general formula (II), except for the case where simultaneously A signifies a single bond linkage, $R_2$ signifies a lower alkoxy group, and $R_3$ signifies an aforementioned unsubstituted or substituted phenyl group. These phenylbutanol derivatives are also useful as tranquilizers, analgesics or sedatives.

Examples of alkyl groups in the aforementioned general formulas (I), (II) and (III) include methyl, ethyl, n-propyl, isopropyl, n-butyl, iso-butyl, or tert.-butyl. Examples of alkoxy groups include methoxy, ethoxy, n-propoxy, iso-propoxy, n-butoxy, iso-butoxy or tert.-butoxy.

Examples of halogen atoms include fluorine, chlorine, bromine or iodine. Examples of alkylamino groups include methylamino, ethylamino, isopropylamino, n-butylamino or the like.

The process of the present invention is illustrated below in detail according to the sequence of reactions.

Step 1. Reduction of benzoylpropionamide

In the present process, the reduction is effected in a suitable organic solvent using various reducing agents. Examples of preferable reducing agents are complex compounds of metal hydrides, and particularly preferred is lithium aluminum hydride, diborane, or sodium borohydride-a halogenated metallic compound. While the reducing agents can be used in a stoichiometric amount or more, the objective phenylbutanol derivatives are obtained generally in high yields. The reaction is conducted at a temperature within a range of 0°C to a boiling point of a solvent, preferably 10° to 100°C. In case a complex compound of metal hydride is used as the reducing agent, the solvents used in the present process include diethyl ether, di-n-butyl ether, tetrahydrofuran, dioxane, methylal, N-ethylmorpholine, diethylene glycol dimethyl ether, ethylene glycol dimethyl ether, etc.

After the reaction is complete, the excess of reducing agent present and the complex compound thereof formed are decomposed by addition of water, an alcohol, ethyl acetate or the like, and then the objective phenylbutanol derivative can be isolated or, if necessary, further purified by recrystallization, etc. If desired, the product can be converted into an acid addition salt thereof by the treatment with a mineral or organic acid. The said salt can be formed with, for example, hydrochloric, sulfuric, phosphoric, hydrobromic, thiocyanic, acetic, propionic, oxalic, citric, malic, tartaric, fumaric, maleic, succinic, glycolic, benzoic, cinnamic, p-aminosalicylic, salicylic, methanesulfonic, ascorbic acids, etc.

By the above-said procedure, phenylbutanol derivatives (II) are obtained in high yields.

Step 2. Oxidation of phenylbutanol derivative

The phenylbutanol derivatives (II) obtained in the above-mentioned step 1 are then oxidized to yield butyrophenone derivatives of the general formula (I) in high yields. In the present invention, various oxidizing agents may be used. Examples of the oxidizing agents used in the present invention include manganese dioxide, chromic acid, chromates, oxygen, ozone, dimethyl sulfoxide, potassium permanganate, osmium oxide, and organic peracids. There may be also employed Oppenauer oxidation, or photo-oxidation. The reaction is generally carried out in water or in an organic solvent at a temperature of 0° to 40°C, and lower or higher temperatures may be used. Examples of the organic solvents used in the present oxidation include petroleum ether, ether, chloroform, carbon tetrachloride, benzene, acetic acid, acetone, pyridine, ethyl acetate, etc.

The resulting objective compound of the general formula (I) can be converted, if necessary, into an acid addition salt thereof by treatment, as in step 1, with a mineral or organic acid.

By the process of the present invention there are synthesized the following compounds:

1-Phenyl-4-(4-hydroxy-4-phenyl-piperidino)-1-butanol
1-(p-Fluorophenyl)-4-[4-hydroxy-4-(p-methylphenyl)-piperidino]-1-butanol
1-(p-Fluorophenyl)-4-[4-(p-chlorophenyl)-4-hydroxypiperidino]-1-butanol
1-(p-Fluorophenyl)-4-[4-hydroxy-4-(m-trifluoromethyl-phenyl)piperidino]-1-butanol
1-(p-Fluorophenyl)-4-[4-hydroxy-4-(p-methoxyphenyl)-piperidino]-1-butanol
1-(p-Fluorophenyl)-4-[4-(2-oxo-1-benzimidazolinyl)-piperidino]-1-butanol
1-(p-Fluorophenyl)-4-[4-(2-oxo-1-benzimidazolinyl)-1,2,3,6-tetrahydro-1-pyridyl]-1-butanol
1-(p-Fluorophenyl)-4-[4-(p-chlorophenyl)-1,2,3,6-tetrahydro-1-pyridyl]-1-butanol
1-(p-Fluorophenyl)-4-[4-(p-chlorophenyl)-4-methoxypiperidino]-1-butanol
1-(p-Fluorophenyl)-4-(4-isopropylaminopiperidino)-1-butanol
1-(p-Fluorophenyl)-4-[4-ethoxy-4-(2-thienyl)-piperidino]-1-butanol
1-(p-Fluorophenyl)-4-[4-(1-piperidyl)piperidino]-1-butanol
1-(p-Fluorophenyl)-4-[4-(4-morpholyl)piperidino]-1-butanol
1-(p-Chlorophenyl)-4-[4-(p-chlorophenyl)-4-hydroxypiperidino]-1-butanol
1-(p-Bromophenyl)-4-[4-(p-chlorophenyl)-4-hydroxypiperidino]-1-butanol
1-(p-Methoxyphenyl)-4-[4-(p-chlorophenyl)-4-hydroxypiperidino]-1-butanol
1-(p-Methylphenyl)-4-[4-(p-chlorophenyl)-4-hydroxypiperidino]-1-butanol
1-(p-Trifluoromethylphenyl)-4-[p-chlorophenyl)-4-hydroxypiperidino]-1-butanol
1-(p-Fluorophenyl)-4-[4-(p-chlorophenyl)piperidino]-1-butanol
1-(p-Fluorophenyl)-4-[3-methyl-4-(p-chlorophenyl)-4-hydroxypiperidino]-1-butanol
γ-(4-Hydroxy-4-phenylpiperidino)-butyrophenone
γ-[4-Hydroxy-4-(p-methylphenyl)piperidino]-p-fluorobutyrophenone
γ-[4-(p-Chlorophenyl)-4-hydroxypiperidino]-p-fluorobutyrophenone
γ-[4-Hydroxy-4-(m-trifluoromethylphenyl)-piperidino]-p-fluorobutyrophenone
γ-[4-Hydroxy-4-(p-methoxyphenyl)piperidino]-p-fluorobutyrophenone
γ-[4-(2-Oxo-1-benzimidazolinyl)piperidino]-p-fluorobutyrophenone
γ-[4-(2-Oxo-1-benzimidazolinyl)-1,2,3,6-tetrahydro-1-pyridyl]-p-fluorobutyrophenone
γ-[4-(p-Chlorophenyl)-4-methoxypiperidino]-p-fluorobutyrophenone
γ-[4-(p-Chlorophenyl)-1,2,3,6-tetrahydro-1-pyridyl]-p-fluorobutyrophenone
γ-(4-Isopropylaminopiperidino)-p-fluorobutyrophenone
γ-[4-Ethoxy-4-(2-thienyl)piperidino]-p-fluorobutyrophenone
γ-[4-(1-Piperidyl)piperidino]-p-fluorobutyrophenone
γ-[4-(4-Morpholyl)piperidino]-p-fluorobutyrophenone
γ-[4-(p-Chlorophenyl)-4-hydroxypiperidino]-p-chlorobutyro-phenone
γ-[4-(p-Chlorophenyl)-4-hydroxypiperidino]-p-bromobutyrophenone
γ-[4-(p-Chlorophenyl)-4-hydroxypiperidino]-p-methoxybutyrophenone
γ-[4-(p-Chlorophenyl)-4-hydroxypiperidino]-p-methylbutyrophenone
γ-[4-(p-Chlorophenyl)-4-hydroxypiperidino]-p-trifluoro-methylbutyrophenone γ-[4-(p-Chlorophenyl)piperidino]-p-fluorobutyrophenone γ-[3-Methyl-4-(p-chlorophenyl)-4-hydroxypiperidino]-p-fluorobutyrophenone.

As described above, the present process is an excellent commercial process because of the simplicity of procedures, high yields, etc.

In case $R_2$ in the formula (II) is a hydroxyl group, two hydroxyl groups are contained in the molecule of the phenylbutanol derivative. When such a compound is subjected to the oxidation of step 2 of the present invention, one of the hydroxyl groups is selectively oxidized into a carbonyl group while the other hydroxyl group, i.e. the hydroxyl represented by $R_2$, remains intact. Such a selective oxidation is an extraordinarily characteristic reaction which can not be expected from prior art.

The benzoylpropionamide derivatives of the general formula (III), which are the starting materials of the present process, are readily synthesized using easily available materials by, for example, the following reaction scheme:

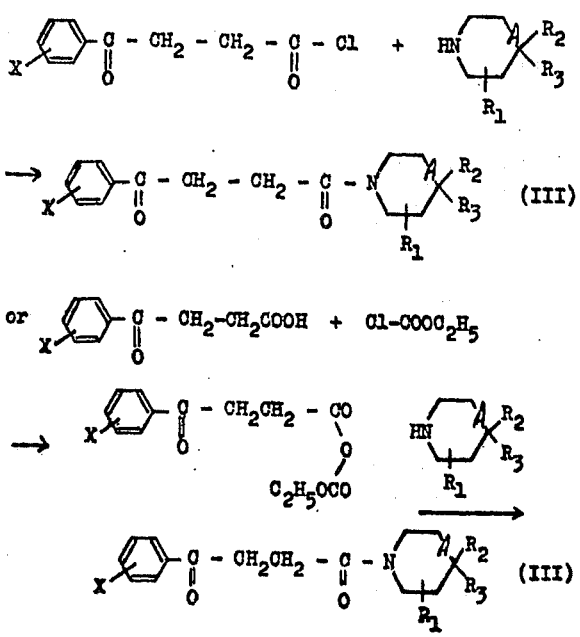

(In the above formulas, A, $R_1$, $R_2$, $R_3$ and X have the same meanings as mentioned above.)

Phenylbutanol derivatives of the general formula (II), in the case where $R^2$ is not an alkoxy group, and acid addition salts thereof are novel and useful compounds having excellent central nervous system activity. They are quite useful as anti-anxiety, anti-psychotonic, anti-emotional, anti-convulsive, anti-psychosis or analgesic drugs.

Each of the pharmaceutically active phenylbutanol compounds of the present invention may be, e.g., incorporated, for oral administration, in tablet as the sole active ingredient. A typical tablet is constituted by from 1 to 2 per cent of a binder, e.g. tragacanth; from 3 to 10 per cent of a lubricant, e.g. talcum; from 0.25 − 1.0 per cent of a lubricant, e.g. magnesium stearate; an average dose of active ingredient; and q.s. 100 per cent of a filler, e.g. lactose. The usual oral dosage is 1 − 100 mg per os daily.

The process for preparing benzoylpropionamide derivatives of the formula (III) is illustrated below in more detail with reference to Referential Examples.

REFERENTIAL EXAMPLE 1

To a solution of 15 g of β-p-fluorobenzoyl-propionic acid and 8.0 g of triethylamine in 100 ml of tetrahydrofuran, was gradually added 8.3 g of ethyl chlorocarbonate while the reaction mixture was kept below 0°C. After being stirred for 25 minutes at a temperature below 0°C, the mixture was added with 6.5 g of piperidine and stirred for another 2 hours. Then the precipitate formed was filtered off and the filtrate was concentrated to dryness under reduced pressure. The residue was recrystallized from hexane to obtain 11 g of 1-(β-p-fluorobenzoylpropionyl)piperidine, melting at 70° − 71°C.

REFERENTIAL EXAMPLES 2–4

According to the procedure similar to that in Referential Example 1, there were obtained the following compounds:

1-[β-(p-Fluorobenzoyl)propionyl]-4-(p-chlorophenyl)-4-hydroxypiperidine, m.p. 151° − 152°C.

1-[1-(β-p-Fluorobenzoylpropionyl)]-4-piperidyl -2-oxobenzimidazoline as colorless crystals, m.p. 205° − 206°C.

1-(β-p-Fluorobenzoylpropionyl)-4-phenyl-1,2,3,6-tetrahydropyridine, m.p. 123° − 124°C.

The present invention is further illustrated below in more detail with reference to Examples, but the scope of the invention is, of course, not limited thereto.

EXAMPLE 1

Step 1

Lithium aluminum hydride (2.2 g) was suspended in 40 ml of tetrahydrofuran and heated to 60°C. A solution of 5.0 g of 1-(β-p-fluorobenzoylpropionyl)piperidine in 10 ml of tetrahydrofuran was added dropwise to said suspension, and heated under reflux for 6 hours with stirring. To the reaction mixture cooled in ice, was gradually added 20 ml of water and the precipitate was filtered off. The filtrate was concentrated to one-third in volume, and extracted with 100 ml of ether. The ether solution was washed with water and dried over anhydrous potassium carbonate, and then gaseous hydrogen chloride was introduced therein. The white precipitate formed was collected by filtration, washed with ether, and recrystallized from ethanol-ether to obtain 4.1 g of 1-(p-fluorophenyl)-4-piperidino-1-butanol hydrochloride, as a white crystalline powder melting at 158° − 159°C.

Step 2

A mixture of 2 g of 1-(p-fluorophenyl)-4-piperidino-1-butanol liberated from the hydrochloride, 20 ml of benzene, and 4 g of a fine powder of manganese dioxide was stirred for 8 hours at room temperature. After filtration, the precipitate was washed with 20 ml of benzene. The benzene washings and filtrate were combined and concentrated under reduced pressure to obtain oily γ-piperidino-p-fluorobutyrophenone (2 g in weight; infrared absorption spectrum, $\nu$ C=O 1678 cm$^{-1}$). The said oily product was dissolved in 20 ml of ether, and gaseous hydrogen chloride was introduced therein to saturation. The precipitate formed was recrystallized from ethanol-ether to yield the hydrochloride melting at 180° − 181°C.

EXAMPLES 2-4

In a similar manner to that of Step 1 in Example 1, there were obtained the compounds listed in Table 1.

Table 1

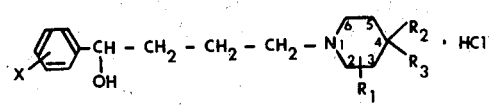

| Example No. | X | $R_1$ | $R_2$ | $R_3$ | Melting point (°C) |
|---|---|---|---|---|---|
| 2 | p-F | H | $CH_3$ | H | 160 – 161 |
| 3 | p-F | 3-$CH_3$ | H | H | 177 – 178 |
| 4 | p-F | H | $OCH_3$ |  | 199 – 200 |

EXAMPLES 5-13

In a similar manner to that of step 2 in Example 1, there were obtained the compounds listed in Table 2.

Table 2

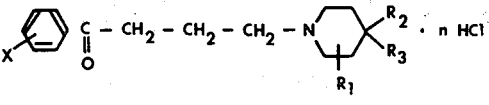

| Example No. | X | $R_1$ | $R_2$ | $R_3$ | n | Melting point.(°C) |
|---|---|---|---|---|---|---|
| 5 | p-Cl | H | H | H | 1 | 200 – 202 |
| 6 | m-$CF_3$ | H | H | H | 1 | 177 – 178 |
| 7 | p-F | H | i-$C_3H_7$ | H | 1 | 208 – 210 |
| 8 | p-F | H | H |  | 2 | 307 – 308 |
| 9 | p-F | H | H |  | 2 | 312 – 315 |
| 10 | p-F | H | $CH_3$ |  | 2 | 270 – 271 |
| 11 | H | H | $OC_2H_5$ |  | 1 | 167 – 169 |
| 12 | H | H | $OC_2H_5$ |  | 1 | 169 – 170 |
| 13 | p-F | H | H |  | 2 | 268 – 270 |

EXAMPLE 14

Step 1

To a mixture of 2.0 g of lithium aluminum hydride and 50 ml of tetrahydrofuran, was gradually added a solution of 5.0 g of 1-[β-(p-fluorobenzoyl)propionyl]-4-(p-chlorophenyl)-4-hydroxypiperidine in 40 ml of tetrahydrofuran. The mixture was stirred at room temperature for one hour, and at 60°to 65°C for 4 hours. Then 15 ml of cold water was added dropwise to the reaction mixture while the mixture was kept below 20°C in an ice bath. The precipitate was filtered off and the tetrahydrofuran was removed from the filtrate by distillation under reduced pressure. The residue was kept cooled for 2 hours and the solid matter was collected by filtration, washed with water, and dried to obtain 1-(p-fluorophenyl)-4-[4-(p-chlorophenyl)-4-hydroxypiperidino]-1-butanol, melting at 128° – 130°C.

Step 2

To a solution of 4.0 g of 1-(p-fluorophenyl)-4-[4-(p-chlorophenyl)-4-hydroxypiperidino]-1-butanol in 100 ml of chloroform was added 10 g of manganese dioxide (fine powder). And then the mixture was stirred at room temperature for 7 hours. The reaction product was filtered and the filtrate was concentrated to dryness under reduced pressure. The residue was recrystallized from aqueous acetone to obtain γ-[4-(p-chlorophenyl)-4-hydroxypiperidino]-p-fluorobutyrophenone, melting at 150° – 151°C.

EXAMPLES 15-19

According to the procedure similar to that in Example 14, there were obtained the following compounds.

Table 3

| Example No. | X | R₁ | R₂ | R₃ | Melting point (°C) |
|---|---|---|---|---|---|
| 15 | p-F | H | OH | (2,6-dichlorophenyl) | 135 – 137 |
| 16 | p-F | H | OH | (2-methylphenyl) | 119 – 120 |
| 17 | p-F | H | OH | (2-methyl-6-chlorophenyl) | 123 – 124 |
| 18 | p-F | H | OH | (2-trifluoromethylphenyl) | 207 – 209 (hydrochloride) |
| 19 | p-F | H | OH | (2-trifluoromethyl-6-chlorophenyl) | 205 – 207 (hydrochloride) |

EXAMPLE 20

One gram of chromium trioxide was added with stirring to 40 ml of pyridine cooled to 0°C. The mixture was stirred at room temperature for 1 hour, and then again cooled to 0°C. Into the said mixture was added 1.1 g of 1-(p-fluorophenyl)-4-[4-hydroxy-4-(p-methylphenyl)-piperidino]-1-butanol, and the mixture was stirred for 1 hour under cooling with ice. The reaction mixture was poured into 300 ml of cold water to separate an oily substance. The oily substance is extracted with ethyl acetate, and the ethyl acetate layer was washed 4 times with each 60 ml of water, dried over anhydrous sodium sulfate, and concentrated to dryness under reduced pressure. The residue was recrystallized from aqueous acetone to obtain γ-(4-hydroxy-4-p-methylphenylpiperidino)-p-fluorobutyrophenone, melting at 119° – 120°C.

EXAMPLE 21

Step 1

To a stirred mixture of 2.0 g of lithium aluminum hydride and 180 ml of tetrahydrofuran at room temperature, was added 4.6 g of 1-[1-(β-p-fluorobenzoylpropionyl)-4-piperidyl]-2-oxobenzimidazoline portionwise over a period of about 10 minutes. The mixture was further stirred at room temperature for one hour, then gradually heated to 60°C over a period of one hour, stirred for additional 4 hours at 60° – 65°C, and then cooled in ice. To the reaction mixture was carefully added 20 milliliters of cold water, and the precipitate formed was filtered off. The filtrate was added with 6 ml of acetic acid, and the tetrahydrofuran was removed by distillation under reduced pressure. The residue was made slightly alkaline by adding a 14% aqueous ammonia, and the solid precipitated was collected by filtration, dried, and recrystallized from toluene to obtain a white crystalline powder of 1-(p-fluorophenyl)-4-[4-(2-oxo-1-benzimidazolinyl)-piperidino]-1-butanol, melting at 160° – 161° C.

Step 2

To a stirred mixture of 4 g of 1-(p-fluorophenyl)-4-[4-(2-oxo-1-benzimidazolinyl)piperidino]-1-butanol and 100 ml of acetone was added dropwise a chromic acid solution (prepared from 2 g of chromic anhydride, 5 ml of water and 2 ml of sulfuric acid) under cooling with ice. The mixture was stirred over night at room temperature, poured into 600 ml of cold water and made alkaline by addition of a 10% aqueous sodium hydroxide solution. The basic material which was separated was extracted twice with each 100 ml of chloroform and the combined extracts were washed with water and evaporated to dryness. Recrystallization of the solid residue from aqueous acetone gave γ-[4-(2-oxo-1-benzimidazolinyl)-piperidino]-p-fluorobutyrophenone, melting at 171° – 172°C.

EXAMPLE 22

To a stirred solution of 2.0 g of 1-(p-fluoro-phenyl)-4-[4-(2-oxo-1-benzimidazolinyl)-1,2,3,6-tetrahydro-1-pyridyl]-1-butanol in 60 ml of chloroform at room temperature, was added portionwise 3.2 g of a fine powder of manganese dioxide. After completion of addition, the mixture was stirred for another 2 hours at room temperature, and the precipitate was filtered off. The filtrate was concentrated to dryness under reduced pressure, and the residue was recrystallized from dioxane containing water, to obtain γ-[4-(2-oxo-1-benzimidazolinyl)-1,2,3,6-tetrahydro-1-pyridyl]-p-fluorobutyrophenone, melting at 146° – 147 5°C.

EXAMPLE 23

In the manner similar to that in Example 22, a compound having the following structural formula was obtained:

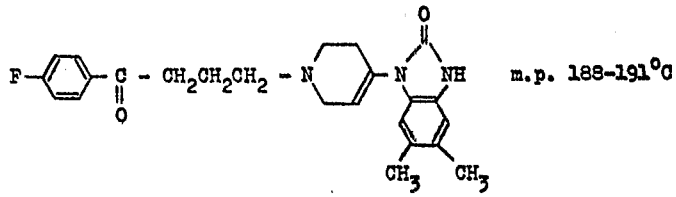

m.p. 188-191°C

EXAMPLE 24

Step 1

To a suspension of 2.2 g of lithium aluminum hydride in 40 ml of tetrahydrofuran was added dropwise a solution of 5.0 g of 1-(62 -p-fluorobenzoylpropionyl)-4-phenyl-1,2,3,6-tetrahydropyridine in 60 ml of tetrahydrofuran over a period of about 30 minutes, during which period a mild evolution of heat was observed.

After completion of the said dropwise addition, the mixture was heated under reflux with stirring for 6 hours. A mixture of 30 ml of water and 70 ml of tetrahydrofuran was added dropwise to the reaction mixture under cooling below 20°C. The precipitate formed was filtered off and the filtrate was concentrated under reduced pressure to remove the tetrahydrofuran. The residue was refrigerated for 2 hours, and the solidified substance was collected by filtration, washed with water, and recrystallized from aqueous ethanol to obtain 4.0 g of 1-(p-fluorophenyl)-4-(4-phenyl-1,2,3,6-tetrahydro-1-pyridyl)-1-butanol, melting at 116° – 117°C. This substance was treated with methanolic hydrogen chloride to yield the hydrochloride melting at 178° – 179°C.

Step 2

To a solution of 2.0 g of 1-p-fluorophenyl-4-(4-phenyl-1,2,3,6-tetrahydro-1-pyridyl)-1-butanol in 30 ml of benzene was added 7 g of a fine powder of manganese dioxide. The mixture was stirred at room temperature for 6 hours, and filtered. The filtrate was concentrated to dryness under reduced pressure, and the residue was recrystallized from aqueous ethanol to obtain γ-(4-phenyl-1,2,3,6-tetrahydro-1-pyridyl)-p-fluorobutrophenone, melting at 123° – 124°C, which was treated with methanolic hydrogen chloride to yield the hydrochloride, melting at 187° – 188°C.

EXAMPLES 25–34

Following the procedure of Example 24, there were obtained the butyrophenone derivatives shown in Table 4.

Table 4

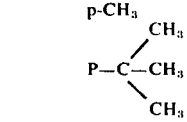

| Example No. | X | R | Melting point (°C) | Melting point of hydrochloride (°C) |
| --- | --- | --- | --- | --- |
| 25 | H | H | | 196 – 197 |
| 26 | H | p-Cl | 131 – 134 | |
| 27 | H | p-CH₃ | | 197 – 198 |
| 28 | H | P—C(CH₃)₃ | | 138 – 141 |
| 29 | m-F | H | | 193 – 195 |
| 30 | p-F | p-F | | 182 – 183 |
| 31 | p-Br | H | | 227 – 229 |
| 32 | p-CH₃ | p-Cl | | 219 – 224 |
| 33 | p-OCH₃ | p-Cl | 138 – 139 | |
| 34 | p-OCH₂CH₃ | H | | 175 – 177 |

What we claim is:

1. 1-(p-Fluorophenyl)-4-[4-(p-chlorophenyl)-4-hydroxy-piperidino]-1-butanol or its non-toxic, pharmaceutically acceptable acid addition salt.

2. 1-(p-Fluorophenyl)-4-(4-hydroxy-4-phenyl-piperidino)-1-butanol or its non-toxic, pharmaceutically acceptable acid addition salt.

3. 1-(p-Fluorophenyl)-4-[4-hydroxy-4-(m-trifluoromethylphenyl)piperidino]-1-butanol or its non-toxic, pharmaceutically acceptable acid addition salt.

4. 1-(p-Fluorophenyl)-4-[4-hydroxy-4-(p-methylphenyl)-piperidino]-1-butanol or its non-toxic, pharmaceutically acceptable acid addition salt.

* * * * *